United States Patent
Wu et al.

(10) Patent No.: US 8,462,333 B2
(45) Date of Patent: Jun. 11, 2013

(54) APPARATUS FOR PERFORMING SERS

(75) Inventors: Wei Wu, Palo Alto, CA (US); Zhiyong Li, Redwood City, CA (US); Shih-Yuan Wang, Palo Alto, CA (US); Michael Josef Stuke, Palo Alto, CA (US); Lars Helge Thylen, Huddinge (SE); Fung Suong Ou, Palo Alto, CA (US); Min Hu, Sunnyvale, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 462 days.

(21) Appl. No.: 12/905,891

(22) Filed: Oct. 15, 2010

(65) Prior Publication Data

US 2012/0092660 A1     Apr. 19, 2012

(51) Int. Cl.
*G01J 3/44*    (2006.01)
(52) U.S. Cl.
USPC .......................................................... 356/301
(58) Field of Classification Search
USPC .......................................................... 356/301
See application file for complete search history.

(56) References Cited

U.S. PATENT DOCUMENTS

| | | | |
|---|---|---|---|
| 7,342,656 B2 * | 3/2008 | Islam et al. .................... | 356/301 |
| 2006/0231381 A1 | 10/2006 | Jensen et al. | |
| 2007/0252136 A1 * | 11/2007 | Lieber et al. .................... | 257/24 |
| 2008/0017845 A1 | 1/2008 | Drndic et al. | |
| 2008/0098805 A1 * | 5/2008 | Jin et al. ......................... | 73/105 |
| 2008/0187648 A1 | 8/2008 | Hart et al. | |
| 2009/0261815 A1 | 10/2009 | Cairns et al. | |
| 2011/0116089 A1 * | 5/2011 | Schmidt et al. ............... | 356/301 |

FOREIGN PATENT DOCUMENTS

EP     2058908 A1     5/2009

OTHER PUBLICATIONS

Michael J. Stuke, Surface Enhanced Raman Spectroscopy Employing Vibrating Nanorods, U.S. Appl. No. 12/697,136, filed Jan. 29, 2010.

Huh Pei Kuo, Vibrating Tip Surface Enhanced Raman Spectroscopy, U.S. Appl. No. 12/697,156, filed Jan. 29, 2010.

Josef Giglmayr, Nano-Finger Electrodes for the Electro-Optical Generation and Tuning of Gratings at Several Wavelengths, <http://www.ipme.ru/ipme/conf/NN2003/NN2003_Abstracts.pdf > Publication Date: Aug. 30, 2003-Sep. 6, 2003.

* cited by examiner

*Primary Examiner* — Tarifur Chowdhury
*Assistant Examiner* — Sunghee Y Gray

(57) ABSTRACT

An apparatus for performing SERS includes a substrate and flexible nano-fingers, each of the nano-fingers having a first end attached to the substrate, a free second end, and a body portion extending between the first end and the second end, in which the nano-fingers are arranged in an array on the substrate. The apparatus also includes an active material layer disposed on each of the second ends of the plurality of nano-fingers, in which the nano-fingers are to be in a substantially collapsed state in which the active layers on at least two of the nano-fingers contact each other under dominant attractive forces between the plurality of nano-fingers and in which the active material layers are to repel each other when the active material layers are electrostatically charged.

20 Claims, 5 Drawing Sheets

APPARATUS FOR PERFORMING SERS

STATEMENT OF GOVERNMENT INTEREST

This invention has been made with government support under Contract No. HR0011-09-3-0002, awarded by Defense Advanced Research Projects Agency. The government has certain rights in the invention.

BACKGROUND

Detection and identification or at least classification of unknown substances has long been of great interest and has taken on even greater significance in recent years. Among advanced methodologies that hold a promise for precision detection and identification are various forms of spectroscopy, especially those that employ Raman scattering. Spectroscopy may be used to analyze, characterize and even identify a substance or material using one or both of an absorption spectrum and an emission spectrum that results when the material is illuminated by a form of electromagnetic radiation (for instance, visible light). The absorption and emission spectra produced by illuminating the material determine a spectral 'fingerprint' of the material. In general, the spectral fingerprint is characteristic of the particular material or its constituent elements facilitating identification of the material. Among the most powerful of optical emission spectroscopy techniques are those based on Raman-scattering.

Raman-scattering optical spectroscopy employs an emission spectrum or spectral components thereof produced by inelastic scattering of photons by an internal structure of the material being illuminated. These spectral components contained in a response signal (for instance, a Raman signal) may facilitate determination of the material characteristics of an analyte species including identification of the analyte.

Unfortunately, the Raman signal produced by Raman-scattering is extremely weak in many instances compared to elastic or Rayleigh scattering from an analyte species. The Raman signal level or strength may be significantly enhanced by using a Raman-active material (for instance, Raman-active surface), however. For instance, the Raman scattered light generated by a compound (or ion) adsorbed on or within a few nanometers of a structured metal surface can be $10^3$-$10^{12}$ times greater than the Raman scattered light generated by the same compound in solution or in the gas phase. This process of analyzing a compound is called surface-enhanced Raman spectroscopy ("SERS"). In recent years, SERS has emerged as a routine and powerful tool for investigating molecular structures and characterizing interfacial and thin-film systems, and even enables single-molecule detection. Engineers, physicists, and chemists continue to seek improvements in systems and methods for performing SERS.

BRIEF DESCRIPTION OF THE DRAWINGS

Embodiments are illustrated by way of example and not limited in the following figure(s), in which like numerals indicate like elements, in which.

DETAILED DESCRIPTION

Figure 1A:
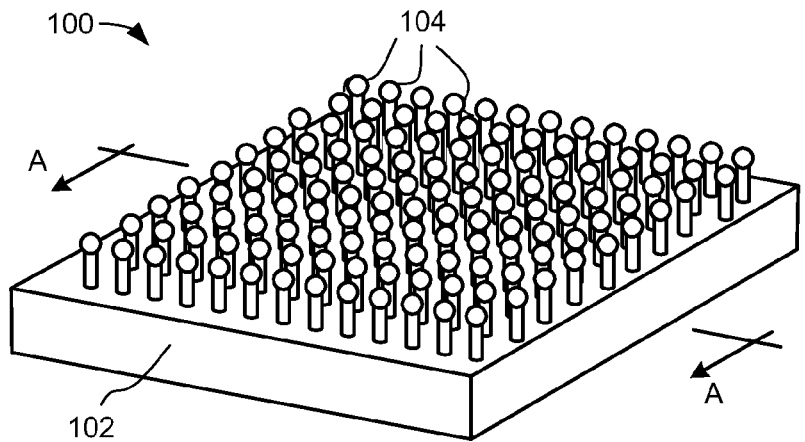
FIG. 1A shows an isometric view of an apparatus for performing SERS, according to an example of the invention.

For simplicity and illustrative purposes, the principles of the embodiments are described by referring mainly to examples thereof. In the following description, numerous specific details are set forth in order to provide a thorough understanding of the embodiments. It will be apparent however, to one of ordinary skill in the art, that the examples may be practiced without limitation to these specific details. In other instances, well known methods and structures are not described in detail so as not to unnecessarily obscure the description of the examples.

Disclosed herein is an apparatus for performing surface enhanced Raman spectroscopy (SERS) to detect at least one molecule in an analyte sample with a relatively high level of precision. In one regard, the accuracy of the molecule detection is relatively high because the apparatus disclosed herein significantly increases the probability that the at least one molecule will be located near or on a Raman-active material layer configured to enhance Raman light emission from the at least one molecule. In another regard, the accuracy is increased because the apparatus disclosed herein enables the signal-to-noise ratio in the processing of the Raman light emissions to be significantly increased.

As discussed in greater detail herein below, the apparatus for performing SERS includes a plurality of flexible nano-fingers that are configured to collapse under dominant attractive forces between the plurality of flexible nano-fingers. In this regard, as the nano-fingers collapse, at least some of the nano-fingers are likely to contact each other, thereby trapping the molecule(s) therebetween. In addition, the tips or free ends of the nano-fingers include Raman-active material layers, and thus, the emission of Raman signals from the molecule(s) trapped in, attached to, or otherwise in the vicinities of the tips of the nano-fingers is likely to be enhanced.

As further discussed in greater detail herein below, active material layers disposed on the free ends of the nano-fingers are electrostatically charged to cause the nano-fingers to be repelled from each other and thereby create gaps into which the analyte molecules are introducible. The active material layers may comprise the Raman-active material layers discussed above or may comprise a separate layer of material from the Raman-active material layers. The electrostatic charge applied to the active material layers may be modulated to thereby enable additional analyte molecules to be introduced and to become trapped between adjacent ones of the nano-fingers. In this regard, the likelihood of identifying the analyte through an analysis of the molecule(s) may substantially be increased. In addition, a Raman scattered light detector may lock in to the frequency at which the positions of the free ends of the nano-fingers are modulated to improve the signal-to-noise ratio of the signals detected from the Raman scattered light emitting from the molecule(s). Moreover, the frequency of modulation may be tuned to further optimize accurate detection of the Raman scattered light.

Throughout the present disclosure, the term "n" following a reference numeral is intended to denote an integer value that is greater than 1. In addition, the terms "a" and "an" are intended to denote at least one of a particular element.

FIG. 1A shows an isometric view of an apparatus 100 for performing SERS configured in accordance with examples of the present invention. It should be understood that the apparatus 100 depicted in FIG. 1A may include additional components and that some of the components described herein may be removed and/or modified without departing from a scope of the apparatus 100. It should also be understood that the components depicted in FIG. 1 are not drawn to scale and thus, the components may have different relative sizes with respect to each other than as shown therein.

The apparatus 100 includes a substrate 102 and a plurality of nano-fingers 104. More particularly, the nano-fingers 104 are depicted as being attached to and extending above a surface of the substrate 102. The nano-fingers 104 may be integrally formed with the substrate 102 or may be separately formed from the substrate 102. Thus, the nano-fingers 104 may be formed of the same material or materials as the substrate 102 or may be formed of one or more different materials from the substrate 102.

A nano-finger 104 may be defined as an elongated, nanoscale structure having a length (or height) that exceeds by more than several times a nanoscale cross sectional dimension (for instance, width) taken in a plane perpendicular to the length (for instance, length>3×width). In general, the length is much greater than the width or cross sectional dimension to facilitate collapsing of the nano-finger 104 laterally onto one or more neighboring nano-fingers 104. In some embodiments, the length exceeds the cross sectional dimension (or width) by more than a factor of about 5 or 10. For example, the width may be about 100 nanometers (nm) and the height may be about 500 nm. In another example, the width at the base of the nano-finger 104 may range between about 20 nm and about 300 nm and the length may be more than about 1 micrometer (μm). In other examples, the nano-finger 104 is sized based upon the types of materials used to form the nano-finger 104. Thus, for instance, the more rigid the material(s) used to form the nano-finger 104, the less the width of the nano-finger 104 may be to enable the nano-finger 104 to be laterally collapsible.

The nano-fingers 104 may be formed of a polymer material, such as, polydimethylsiloxane (PDMS) elastomer, polyimide, polyethylene, polypropelene, etc., to thus cause the nano-fingers 104 to be relatively flexible and thus to be laterally collapsible. In various examples, the nano-fingers 104 may be fabricated through a nanoimprinting process in which a template of relatively rigid pillars is employed in a multistep imprinting process on a polymer matrix to form the nano-fingers 104. Various other processes, such as, etching, and various techniques used in the fabrication of micro-electromechanical systems (MEMS) and nano-electromechanical systems (NEMS) may also be used to fabricate the nano-fingers 104.

As shown in FIG. 1A, the nano-fingers 104 are arranged in an array on the substrate 102. In addition, the nano-fingers 104 may be randomly distributed or the nano-fingers 104 may be arranged in a predetermined configuration to therefore cause the nano-scale protrusions 104 to be distributed in a substantially uniform density on the substrate 102. In any regard, and as discussed in greater detail herein below, the nano-fingers 104 are arranged with respect to each other such that the free ends of at least two neighboring nano-fingers 104 are able to touch each other when the nano-fingers 104 are in a collapsed state. By way of particular example, the neighboring nano-fingers 104 are positioned less than about 100 nanometers apart from each other.

The nano-fingers 104 have been depicted in FIG. 1A as having substantially cylindrical cross-sections. It should, however, be understood that the nano-fingers 104 may have other shaped cross-sections, such as, for instance, rectangular, square, triangular, etc. In addition, or alternatively, the nano-fingers 104 may be formed with one or more features, such as, notches, bulges, etc., to substantially cause the nano-fingers 104 to be inclined to collapse in a particular direction. Thus, for instance, two or more adjacent nano-fingers 104 may include the one or more features to increase the likelihood of these nano-fingers 104 to collapse toward each other.

The substrate 102 provides a support on which the distances between the first ends or bases of the nano-fingers 104 may substantially be maintained. According to an example, the substrate 102 is composed of an insulating material or a dielectric material, including a polymer, glass, $SiO_2$, $Al_2O_3$, or any other suitable material upon which the nano-fingers 104 may be supported. According to another example, the substrate 102 is composed of an electrically conductive material and may operate as an electrically conductive source to the nano-fingers 104 as discussed herein below.

Figure 1B:
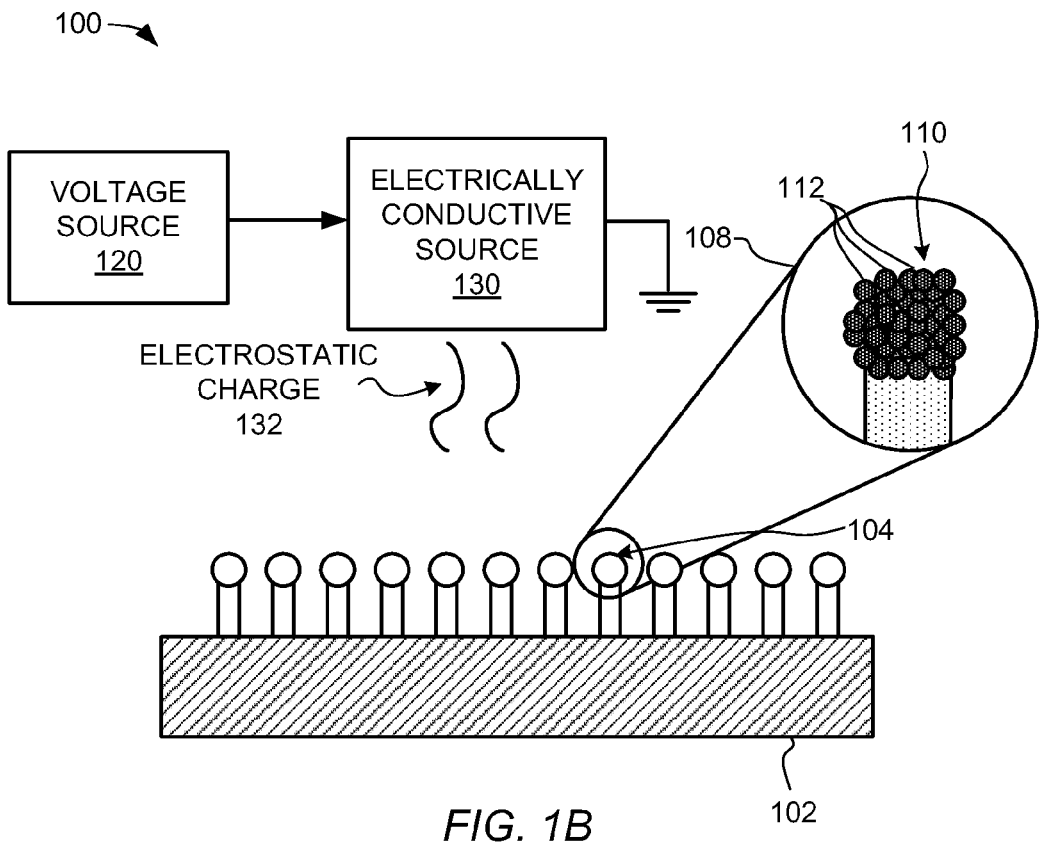
FIGS. 1B and 1C, respectively, show cross-sectional views along a line A-A, shown in FIG. 1A of the apparatus, according to examples of the invention.

Turning now to FIG. 1B, there is shown a cross-sectional view along a line A-A, shown in FIG. 1A, of the apparatus 100, in accordance with an embodiment of the present invention. In addition, an end of a nano-finger 104 is magnified in an enlargement 108, which reveals that the nano-finger 104 includes an active material layer 110 disposed on the outer surface, near the tip or free end, of the nano-finger 104. Generally speaking, the active material layer 110 comprises a material configured to be electrostatically charged, such as, a metal. According to one or more examples, the active material layer 110 comprises a SERS-active material, such as, the SERS-active nano-particles 112 depicted in FIG. 1B. According to other examples, the active material layer 110 comprises a separate layer, for instance, positioned underneath the nano-particles 112 depicted in FIG. 1B. In these examples, the active material layer 110 may be fabricated as part of and integrated with the nano-finger 104.

Each of the other nano-fingers 104 includes the active material layer 110/SERS-active nano-particles 112 as represented by the circles on the tops or free ends of the nano-fingers 104. Although the enlargement 108 depicts the nano-particles 112 as covering the entire tip of the nano-finger 104, it should be understood that examples of the apparatus 100 may be implemented with gaps between some of the nano-particles 112.

It should also be noted that examples of the apparatus 100 are not limited to nano-particles 112 disposed over just the tips of the nano-scale protrusions 104. In other examples, the nano-particles 112 may be disposed over part of or nearly the entire surface of the nano-fingers 104. In any regard, the SERs-active nano-particles 112 may be deposited onto at least the free ends of the nano-fingers 104 through, for instance, physical vapor deposition (PVD), chemical vapor deposition (CVD), sputtering, etc., of metallic material, or self-assembly of pre-synthesized nano-particles. By way of example, the angle at which the nano-particles 112 are deposited onto the free second ends of the nano-fingers 104 may be controlled to thereby substantially control the deposition of the nano-particles 112.

In addition, the active material layer 110/nano-particles 112 may be configured to one or both of enhance Raman scattering and facilitate analyte adsorption. For instance, the active material layer 110/nano-particles 112 may comprise a Raman-active material such as, but not limited to, gold (Au), silver (Ag), and copper (Cu) having nanoscale surface roughness. Nanoscale surface roughness is generally characterized by nanoscale surface features on the surface of the layer(s) and may be produced spontaneously during deposition of the Raman-active material layer(s). By definition herein, a Raman-active material is a material that facilitates Raman scattering and the production or emission of the Raman signal from an analyte adsorbed on or in a surface layer or the material during Raman spectroscopy.

In some examples, the active material layer 110/nano-particles 112 may be annealed or otherwise treated to increase nanoscale surface roughness of the active material layer 110/nano-particles 112 after deposition. Increasing the surface roughness may enhance Raman scattering from an adsorbed analyte, for example. Alternatively, the arrangement of the nano-particles 112 may provide a nanoscale roughness that enhances Raman scattering, for example.

In some embodiments, a surface of the nano-fingers 104 may be functionalized to facilitate adsorption of the analyte. For example, the tips or free ends of the nano-fingers 104 in a vicinity thereof (not illustrated) may be functionalized with a binding group to facilitate binding with a specific target analyte species. A surface of the active material layer 110/nano-particles 112 may be functionalized, for example. The functionalized surface (that is, either a surface of the nano-finger 104 itself, the active material layer 110/nano-particles 112, or both) may provide a surface to which a particular class of analytes is attracted and may bond or be preferentially adsorbed. The functionalized surface may selectively bond with protein, DNA or RNA, for example.

Also shown in FIG. 1B are a voltage source 120 and an electrically conductive source 130, which is depicted as being connected to a ground. The voltage source 120 may comprise any suitable source from which alternating current (AC) or direct current (DC) voltage may be received. The electrically conductive source 130 may comprise any suitable component through the AC or DC voltage may be applied in relatively close proximity to the nano-fingers 104. Thus, for instance, the electrically conductive source 130 may comprise an electrode or wire positioned in relatively close proximity, without contacting, the nano-fingers 104.

Figure 1C:
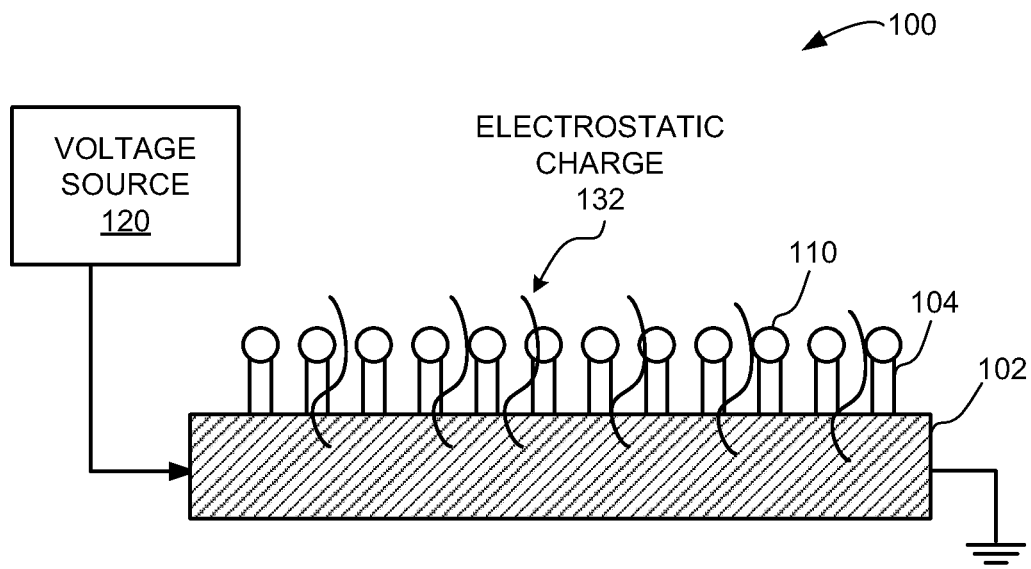

Alternatively, the substrate 102 itself may comprise the electrically conductive source 130 as depicted in FIG. 1C. In the embodiment depicted in FIG. 1C, the nano-fingers 104 are formed of at least a semi-insulating material to thereby substantially limit or prevent conduction of electrical charge from the substrate 102 to the active material layers 110/nano-particles 112 through the nano-fingers 104.

In FIGS. 1A-1C, the voltage source 120 is depicted as being activated or in an on state and is thus depicted as applying a voltage through the electrically conductive source 130 or the substrate 102. The application of the voltage through the electrically conductive source 130 is depicted as generating an electrostatic charge 132 onto the active material layer 110/nano-particles 112, thereby causing the active material layer 110/nano-particles 112 to become electrostatically charged with the same polarity. The nano active material layer 110/nano-particles 112 disposed on the ends of adjacent nano-fingers 104 thus repel each other.

Although the nano-fingers 104 have been depicted in FIGS. 1A-1C as each extending vertically and at the same heights with respect to each other, it should be understood that some or all of the nano-fingers 104 may extend at various angles and heights with respect to each other. The differences in angles and/or heights between the nano-fingers 104 may be based upon, for instance, differing levels of influence the neighboring active material layer 110/nano-particles 112 apply on the active material layer 110/nano-particles 112 of the nano-fingers 104, differences arising from the fabrication of the nano-fingers 104 and the deposition of the nano-particles 112 on the nano-fingers 104, etc.

Figure 2A:
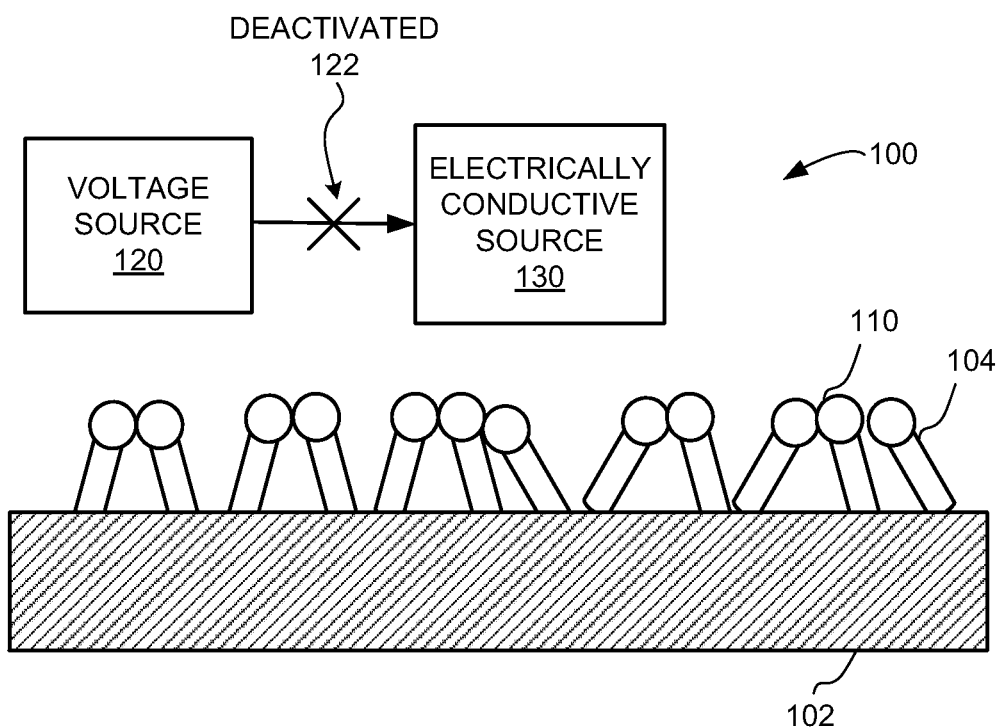
FIG. 2A shows a cross-sectional side view along a line A-A, shown in FIG. 1A when the nano-particles of a plurality of nano-fingers are not electrostatically charged, according to another example of the invention.

However, when the voltage source 120 is deactivated, as indicated by the "X" 122 in FIG. 2A, the nano-fingers 104 are configured to be in a substantially collapsed state. The substantially collapsed state is one in which the active material layer 110/nano-particles 112 of adjacent nano-fingers 104 are configured to be drawn together through static force similar to the manner in which thin layers of gold leaf are drawn together when brought in relatively close proximity to each other. In addition or alternatively, the substantially collapsed state is one in which the nano-fingers 104 collapse by virtue of gravitational force acting on the nano-fingers 104.

Although the nano-fingers 104 have been depicted in FIG. 2A as collapsing at respective first ends attached to the substrate 102, it should be understood that the nano-fingers 104 may collapse along other locations throughout the body portions of the nano-fingers 104. Thus, for instance, one or more of the nano-fingers 104 may be in the collapsed state by bending at around a central position of the body portions, such as occurs with a relatively thin wire or human hair. The locations at which the nano-fingers 104 bend and therefore collapse may substantially be random and due to the properties of the materials used to form the nano-fingers 104 as well as the materials and amounts of the active material layer 110/nano-particles 112 deposited on the nano-fingers 104. In addition, or alternatively, the nano-fingers 104 may employ one or more features designed to promote the collapsing of the nano-fingers 104 when the active material layer 110/nano-particles 112 are not electrostatically charged with the same polarity. The one or more features may include, for instance, inclusion of additional material or active material layer 110/nano-particles 112 on one side of a nano-finger 104 to make the weight distribution of the nano-finger 104 uneven, the formation of a notch or other feature on one side of the nano-finger 104 to promote collapsing of the nano-finger 104 toward that side, etc. According to an example, the one and more features may be employed on the nano-fingers 104 to promote the collapsing of a plurality of adjacent nano-fingers 104 toward each other.

Figure 2B:
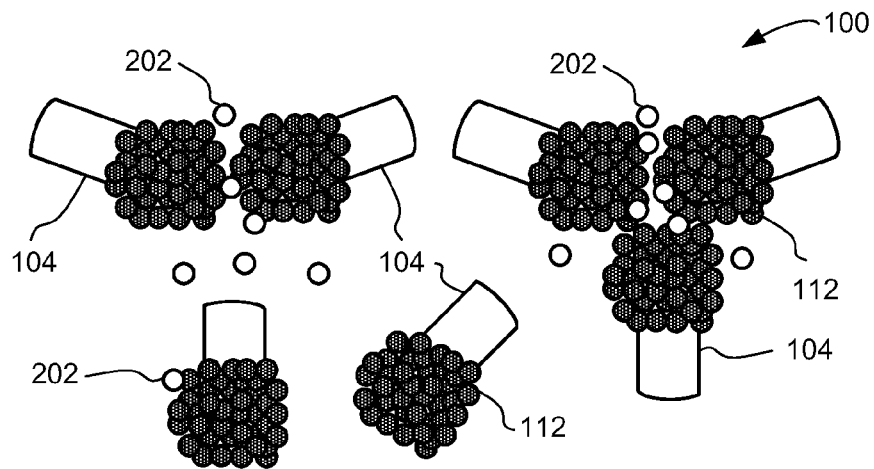
FIG. 2B shows a top view of the apparatus 100 depicted in FIG. 2A, according to an example of the invention.

An example of an enlarged top view of part of the apparatus 100 depicted in FIG. 2A, in which the nano-fingers 104 are in the collapsed state, is depicted in FIG. 2B. As shown in FIG. 2B, the nano-fingers 104 may collapse in any of a number of different directions. More particularly, two of the nano-fingers 104 in the upper left portion of FIG. 2B are depicted as having collapsed toward each other, while the bottom two nano-fingers 104 are depicted as having collapsed away from other nano-fingers 104. In addition, three of the nano-fingers 104 on the right portion of FIG. 2B are depicted as having collapsed toward each other. It should be clearly understood that adjacent nano-fingers 104 may have collapsed in any other possible arrangement. It should also be clearly understood that the nano-fingers 104 may be configured to collapse in random or predefined directions following activation and deactivation of the voltage source 120, as discussed above with respect to FIG. 2A.

Also shown in FIG. 2B are a plurality of analyte molecules 202 that may be introduced onto the apparatus 100 in a fluid or a gas. In addition, some of the analyte molecules 202 are depicted as being captured between the nano-particles 112 of adjacent nano-fingers 104 that have collapsed upon each other, while others of the analyte molecules 202 have been depicted as being unattached to any of the nano-particles 112. Other ones of the analyte molecules 202 have been depicted as being attached to the nano-particles 112. As such, some of the analyte molecules 202 may be adsorbed by the nano-particles 112.

The active material layer 110/nano-particles 112 may be electrostatically charged to cause adjacent ones of the nano-fingers 104 to be repelled from each other and thereby create sufficiently sized gaps therebetween to enable the analyte molecules 202 to be introduced into the gaps. In addition, the electrostatic charge on the active material layer 110/nano-particles 112 may be removed, to thereby cause at least some of the nano-fingers 104 to collapse on each other as shown in FIGS. 2A and 2B and thereby trap the analyte molecules 202 between the adjacent nano-fingers 104 that have collapsed upon each other. The trapping of the analyte molecules 202 between the adjacent nano-fingers 104 may enhance a signal strength of a Raman signal produced by Raman scattering from the analyte molecules 202 due to their close proximity to the nano-particles 112. The trapping of the analyte molecules 202 also increases the likelihood that Raman light scattering from the analyte molecules 202 will be enhanced by the nano-particles 112.

Figure 3:
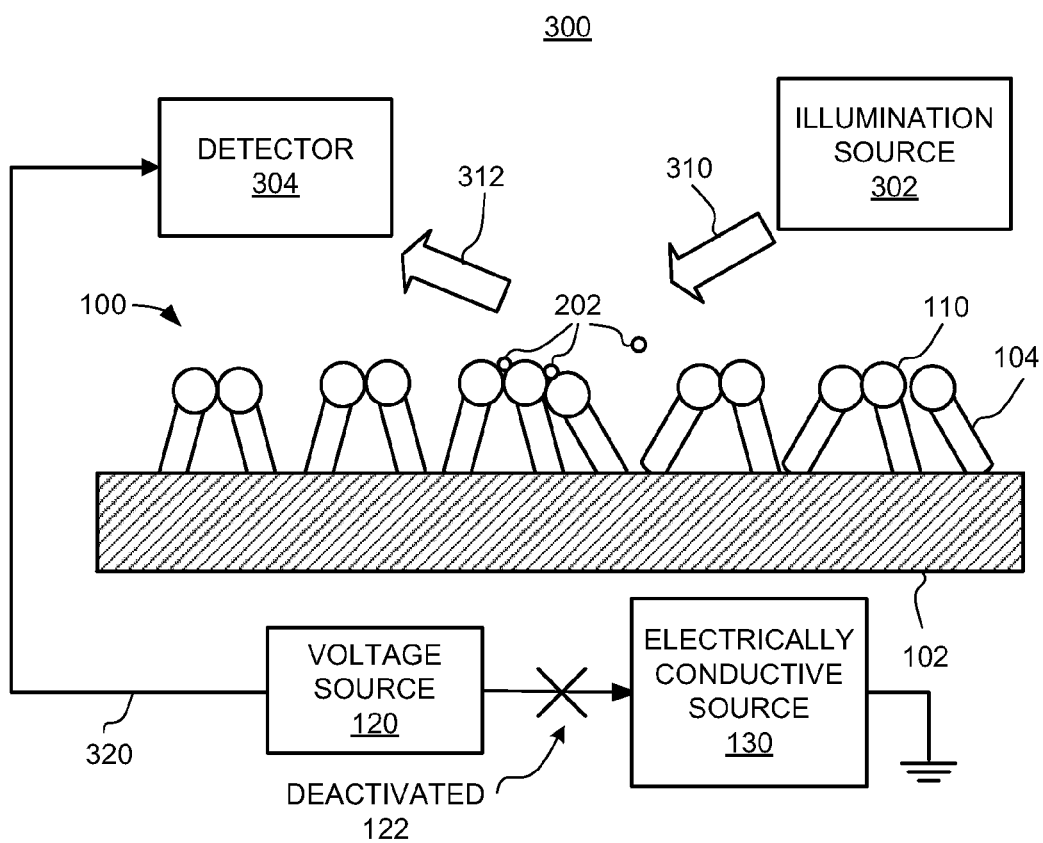
FIG. 3 shows a block diagram of a SERS system employing the apparatus depicted in FIGS. 1A-2B, according to an example of the invention.

With reference now to FIG. 3, there is shown a block diagram of a surface enhanced Raman spectroscopy (SERS) system 300, according to an embodiment. It should be understood that the system 300 depicted in FIG. 3 may include additional components and that some of the components described herein may be removed and/or modified without departing from a scope of the system 300. It should also be understood that the components depicted in FIG. 3 are not drawn to scale and thus, the components may have different relative sizes with respect to each other than as shown therein.

As shown in FIG. 3, the SERS system 300 includes the apparatus 100 depicted in FIGS. 1A-1C and 2A-2B, an illumination source 302 and a detector 304. The voltage source 120 and the electrically conductive source 130 are also depicted in FIG. 3. The apparatus 100 is also depicted as including the active material layer 110/nano-particles 112 disposed on the nano-fingers 104, which is attached to the substrate 102. As discussed above, according to an example, the substrate 102 may comprise the electrically conductive source 130, and thus, the electrically conductive source 130 may be omitted from the system 300 and the voltage source 120 may be configured to apply a voltage through the substrate 102.

The SERS system 300 is depicted with the voltage source 120 in a deactivated state, and thus, the active material layer 110/nano-particles 112 are not electrostatically charged. As such, the nano-fingers 104 are depicted as being in a collapsed state in FIG. 3 and thus, one or more analyte molecules 202 may be trapped between two or more of the contacting nano-fingers 104.

The illumination source 302 is configured to emit an electromagnetic radiation, such as, visible light, onto the free ends of the nano-fingers 104, as represented by the arrow 310. By way of example, the illumination source 302 may comprise a laser that illuminates the free ends of the nano-fingers 104 with visible light. The electromagnetic radiation is intended to cause the analyte molecules 202 to produce Raman scattered light as represented by the arrow 312. In addition, the detector 304 is positioned and configured to detect the Raman scattered light emitting from the analyte molecule(s) 202.

As discussed above, the nano-particles 112 located near or adjacent to the analyte molecule(s) 202 may enhance the production of Raman scattered light from the analyte molecule(s) 202 by concentrating or otherwise enhancing an electromagnetic field in a vicinity of the analyte molecule(s) 202. As also discussed above, the collapsing of two or more of the nano-fingers 104 upon each other to trap the analyte molecule(s) 202 may substantially increase the likelihood that the analyte molecule(s) 202 will be positioned near or in contact with some nano-particles 112. In this regard, the likelihood that an analyte molecule(s) 202 will produce relatively strong Raman scattered light will thus also be increased. Thus, through implementation of the system 300, the detector 304 may receive a relatively stronger Raman scattered light signal 312 from the illuminated analyte molecule(s) 202 as compared with conventional SERS systems.

The detector 304 is configured to convert the Raman scattered light 312 emitted from the analyte molecule(s) 202 into electrical signals that may be processed to identify, for instance, the analyte. In some examples, the detector 304 is configured to output the electrical signals to other components (not shown) configured to process the electrical signals. In other examples, the detector 304 is equipped with processing capabilities to identify the analyte.

According to one or more examples, the voltage source 120 is configured to modulate application of voltage through the electrically conductive source 130 or the substrate 102 at a defined frequency. In this regard, the voltage source 120 is configured modulate the electrostatic charging of the nano-particles 110 to thereby cause the nano-fingers 104 to alternately be in the collapsed state when the active material layer 110/nano-particles 112 are not electrostatically charged and in a repelled state with respect to each other when the active material layer 110/nano-particles 112 are electrostatically charged. In these examples, the detector 304 may be programmed with or be able to identify the defined frequency at which the voltage source 120 modulates application of the voltage.

In addition, the detector 304 or a post-signal processing apparatus (not shown) located downstream of the detector 304, may implement a lock-in detection technique on the detected Raman light emission 312 at the identified frequency. As such, for instance, the detector or post-signal processing apparatus includes a lock-in amplifier, a boxcar amplifier, or the like, which serves to detect and amplify only the signal component of the electrical signal from the detector 304 that has the same frequency as that of the identified frequency at which the voltage source 120 modulates the application of voltage through the electrically conductive source 130. Because the detector 304 or the post-signal processing apparatus detects and amplifies only the signal component of the electrical signal that has the same frequency as that of the identified frequency of a reference signal 320 received from the voltage source 120, the input signal component having a frequency different from that of the reference signal 320 is not sampled. Further, by selecting appropriately the locked-in phase, the detector 304 or the post-signal processing apparatus may sample the signal component ascribable to a particular analyte molecule 202.

Through implementation of the lock-in detection technique discussed above, the signal-to-noise ratio in the processing of the Raman light emissions 312 may be significantly increased over conventional Raman light emission detection techniques. As such, the accuracy of the molecule detection may also be significantly increased over conventional Raman light emission detection techniques.

Figure 4:
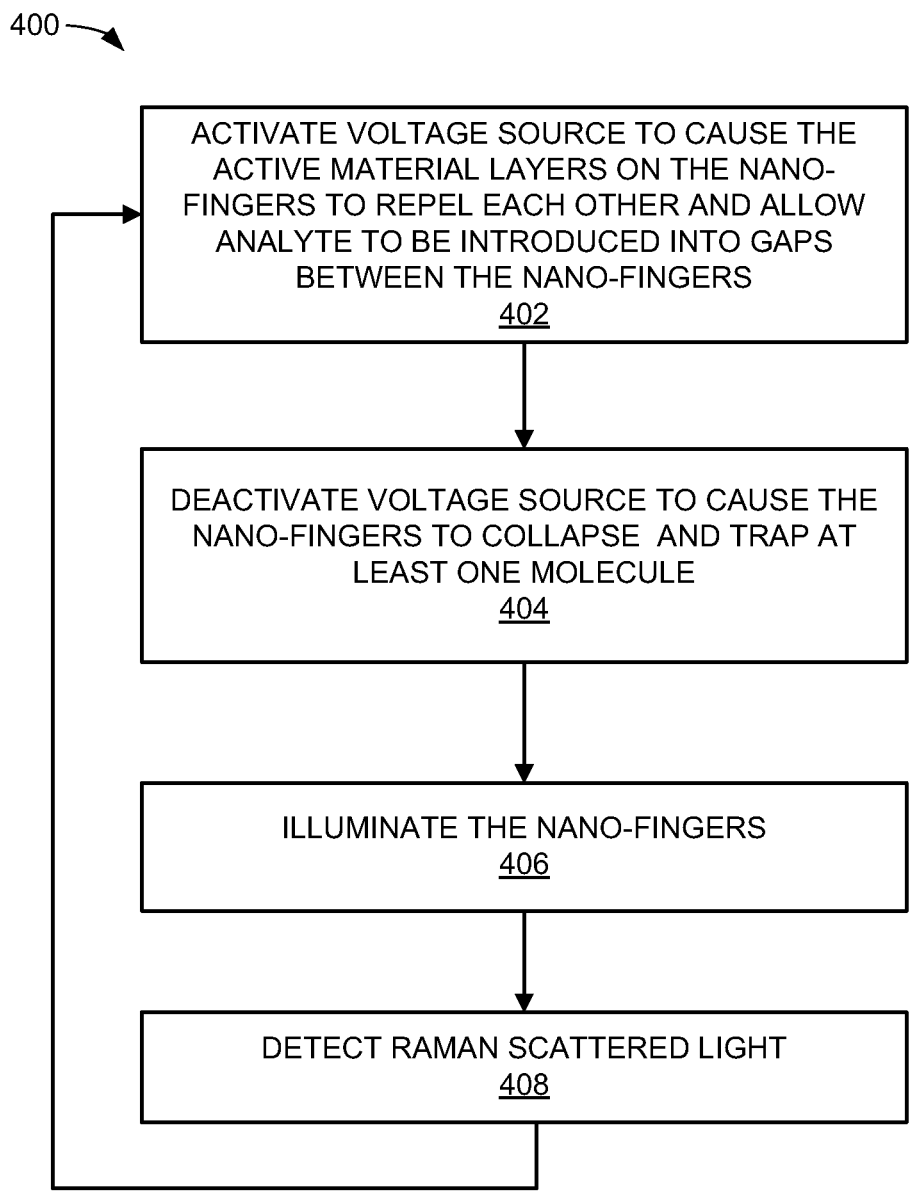
FIG. 4 shows a flow diagram of a method for performing SERS to detect at least one analyte molecule on the apparatus employing the SERS system depicted in FIG. 3, according to an example of the invention.

Turning now to FIG. 4, there is shown a flow diagram of a method 400 for performing surface enhanced Raman spectroscopy (SERS) to detect at least one analyte molecule 202 on an apparatus 100, according to an embodiment. It should be understood that the method 400 depicted in FIG. 4 may include additional steps and that some of the steps described herein may be removed and/or modified without departing from a scope of the method 400.

At block 402, the voltage source 120 is activated to apply a voltage through the electrically conductive source 130 and cause the active material layer 110/nano-particles 112 to become electrostatically charged with the same polarity. The electrostatically charged nano-particles 110 are thus configured to obtain the same charge and repel each other as discussed above with respect to FIGS. 1A-1C. In addition, gaps are created between adjacent ones of the nano-fingers 104 into which the analyte molecules 202 may be introduced. According to an example, the nano-fingers 104 are arranged at a range of distances with respect to each other in which the electrostatic charge on the active material layer 110/nano-particles 112 of adjacent nano-fingers 104 is sufficiently strong to cause the active material layer 110/nano-particles 112 to be repelled from each other a sufficient distance to enable at least one molecule of the analyte to enter between the active material layer 110/nano-particles 112 on the adjacent nano-fingers 104 and to be sufficiently close to each other to enable the active material layer 110/nano-particles 112 on adjacent nano-fingers 104 to contact each other when the nano-fingers 104 are in the collapsed state.

In one example, the analyte is introduced onto the nano-fingers 104 prior to initiation of the method 400. In another example, the analyte is introduced onto the nano-fingers 104, for instance, through introduction through a micro-fluidic channel (not shown), following initiation of the method 400 and more particularly, following step 402.

At block 404, the voltage source 120 is deactivated to remove the electrostatic charge of the same polarity on the active material layer 110/nano-particles 112 and therefore enable the nano-fingers 104 to collapse as the active material layer 110/nano-particles 112 no longer repel each other. As the nano-fingers 104 collapse, at least some of the nano-fingers 104 are likely to collapse on each other such that the active material layer 110/nano-particles 112 on one nano-finger 104 contacts the active material layer 110/nano-particles 112 on an adjacent nano-finger 104. The contacting of the second ends of the nano-fingers 104 may occur because the apparatus 100 may include a relatively large number of closely arranged nano-fingers 104 and based upon a random collapsing of the nano-fingers 104, at least two of the second ends are highly likely to contact each other when the nano-fingers 104 are in the collapsed state. Alternatively, however, and as discussed above, at least some of the nano-fingers 104 may be provided with one or more features designed to cause the nano-fingers 104 to collapse toward each other, thereby increasing the likelihood and the number of nano-fingers 104 coming into contact with each other when the nano-fingers 104 are in the collapsed state.

At block 406, the illuminating source 302 is activated to illuminate the second ends of the nano-fingers 104. As discussed above, the nano-particles 112 are configured to enhance the production of Raman scattered light emitted from the analyte molecules 202. The probability that the Raman scattered light production from the analyte molecules 202 will be enhanced is generally increased for those analyte molecule(s) 202 that are trapped between the second ends of one or more adjacent nano-fingers 104.

At block 408, the detector 304 detects the Raman scattered light, if any, produced from the analyte molecule(s) 202. As discussed above, the detected Raman scattered light may be processed to identify the analyte.

According to an example, the method 400 may end following detection of the Raman scattered light at block 408. According to another example, however, blocks 402-408 of the method 400 may be performed over a number of cycles to further enhance the likelihood of detecting sufficiently strong signals to accurately identify the analyte. In addition, as discussed above with respect to the detector 304 in FIG. 3, the voltage source 120 may be modulated between activation at block 402 and deactivation at block 404 at a defined frequency. Moreover, the detector 304 or a processor configured to receive and process electrical signals from the detector 304 is configured to lock into the defined frequency at which the voltage source 120 is activated and deactivated to substantially enhance the signal-to-noise ratio of the electrical signals converted from the Raman light emission 312 detected by the detector 304. More particularly, for instance, the detector 304 may be configured to determine the moment that the second ends of the nano-fingers 104 collapse on each other from the defined frequency to detect the Raman light emission 312 or to process the electrical signal converted from the Raman light emission 312 at that moment since that is when the Raman signal emitted from the analyte molecule(s) 202 is likely to be the greatest. In this regard, the sensitivity of the detector 304 to the Raman light emission 312 may substantially be increased.

According to one or more examples, the frequency at which the voltage source 120 is modulated may be tuned to obtain the optimal or nearly optimal SERS performance. Thus, for instance, the frequency at which the voltage source 120 is modulated may be decreased to provide additional time for the analyte molecules to be introduced between adjacent nano-fingers 104. Alternatively, the frequency may be increased to enable a greater number of signal detections to be obtained over a period of time.

Figure 5:
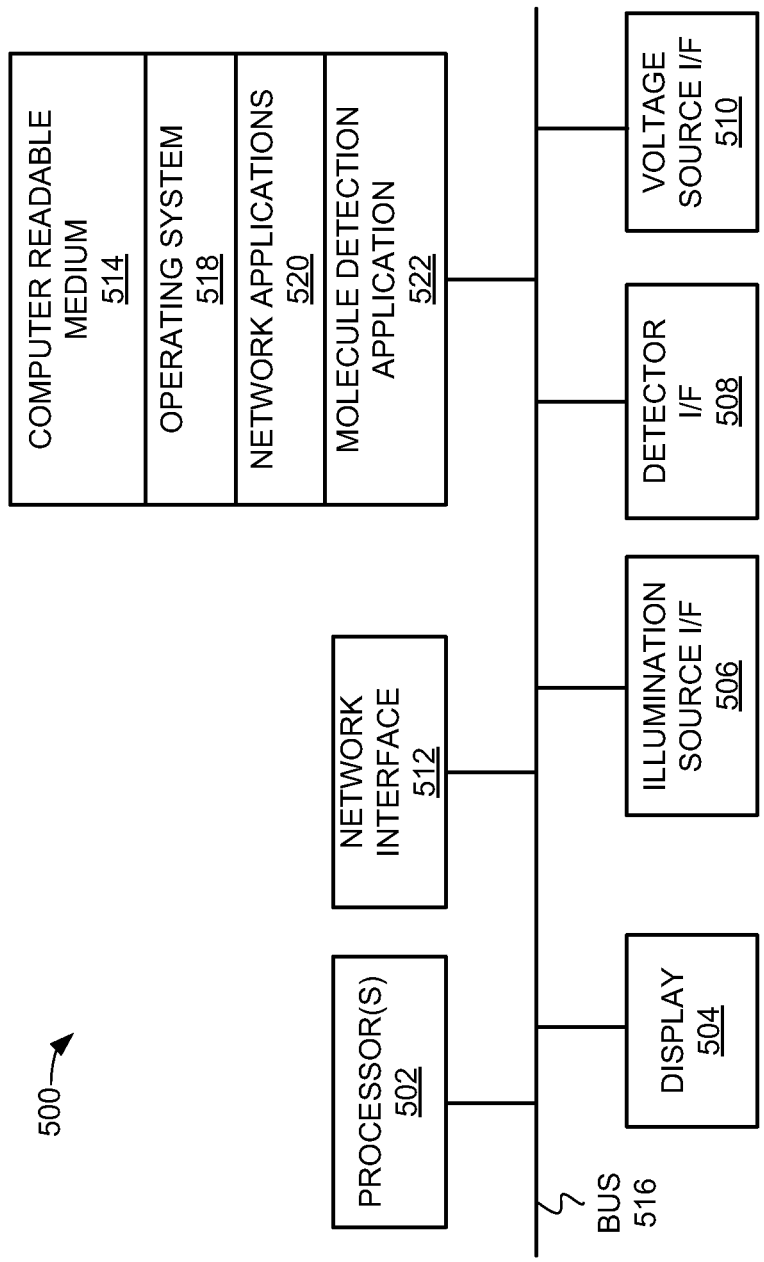
FIG. 5 shows a schematic representation of a computing device configured to implement the method depicted in FIG. 4, according to an example of the invention.

Turning now to FIG. 5, there is shown a schematic representation of a computing device 500 configured to implement or execute the method 400, in accordance with examples of the invention. The computing device 500 may comprise, for instance, a desktop computer, laptop, server, etc. The computing device 500 includes one or more processors 502, such as a central processing unit; one or more display devices 504, such as a monitor; an illumination source interface (I/F) 506; a detector interface 508; a voltage source interface 510; one or more network interfaces 512, such as a Local Area Network LAN, a wireless 802.11x LAN, a 3G mobile WAN or a WiMax WAN; and one or more computer-readable mediums 514. Each of these components is operatively coupled to one or more buses 516. For example, the bus 516 may be an EISA, a PCI, a USB, a FireWire, a NuBus, or a PDS.

The computer readable medium 514 may be any suitable medium that participates in providing instructions to the processor 502 for execution. For example, the computer readable medium 510 may be non-volatile media, such as an optical or a magnetic disk; volatile media, such as memory; and transmission media, such as coaxial cables, copper wire, and fiber optics. Transmission media can also take the form of acoustic, light, or radio frequency waves.

The computer-readable medium 510 may also store an operating system 518, such as Mac OS, MS Windows, Unix, or Linux; network applications 520; and a molecule detection application 522. The operating system 518 may be multi-user, multiprocessing, multitasking, multithreading, real-time and the like. The operating system 518 may also perform basic tasks such as recognizing input from input devices, such as a keyboard or a keypad; sending output to the display 504, the illuminating source 302, the detector 304, and the voltage source 120; keeping track of files and directories on medium 514; controlling peripheral devices, such as disk drives, printers, image capture device; and managing traffic on the one or more buses 516. The network applications 520 include various components for establishing and maintaining network connections, such as software for implementing communication protocols including TCP/IP, HTTP, Ethernet, USB, and FireWire.

The molecule detection application 522 provides various software components for detecting molecules 202, as described above. In certain examples, some or all of the processes performed by the molecule detection application 522 may be integrated into the operating system 518. In certain embodiments, the processes can be at least partially implemented in digital electronic circuitry, or in computer hardware, firmware, software, or in any combination thereof.

What has been described and illustrated herein is an example along with some of its variations. The terms, descriptions and figures used herein are set forth by way of illustration only and are not meant as limitations. Those skilled in the art will recognize that many variations are possible within the spirit and scope of the subject matter, which is intended to be defined by the following claims—and their equivalents—in which all terms are meant in their broadest reasonable sense unless otherwise indicated.

What is claimed is:

1. An apparatus for performing surface enhanced Raman spectroscopy (SERS), said apparatus comprising:
    a substrate;
    a plurality of flexible nano-fingers, each of the plurality of nano-fingers having a first end attached to the substrate, a free second end, and a body portion extending between the first end and the second end, wherein the plurality of nano-fingers are arranged in an array on the substrate; and
    an active material layer disposed on each of the second ends of the plurality of nano-fingers,
    wherein the plurality of nano-fingers are to be in a substantially collapsed state in which the active layers on at least two of the nano-fingers contact each other under dominant attractive forces between the plurality of nano-fingers and wherein the active material layers are configured to repel each other when the active material layers are electrostatically charged.

2. The apparatus according to claim 1, further comprising:
    an electrically conductive source through which a voltage is to be conducted to electrostatically charge the plurality of active material layers.

3. The apparatus according to claim 2, wherein the electrically conductive source is to be supplied with the voltage by a voltage source, and wherein the voltage source is to modulate application of the voltage through the electrically conductive layer at a defined frequency.

4. The apparatus according to claim 2, wherein the substrate comprises the electrically conductive source.

5. The apparatus according to claim 4, wherein each of the plurality of nano-fingers is formed of at least a semi-insulating material to thereby substantially limit or prevent conduction of electrical charge from the substrate to the plurality of active material layers.

6. The apparatus according to claim 1, wherein each of the plurality of nano-fingers is formed of a relatively flexible polymer material.

7. The apparatus according to claim 1, wherein the plurality of nano-fingers have a feature designed to promote the collapsing of the plurality of nano-fingers when the plurality of active material layers are not electrostatically charged.

8. The apparatus according to claim 7, wherein the feature further promotes the collapsing of a plurality of adjacent nano-fingers toward each other.

9. The apparatus according to claim 1, wherein the plurality of nano-fingers are arranged sufficiently close to each other to cause the active material layers disposed on neighboring second ends to contact each other under dominant attractive forces between the neighboring plurality of nano-fingers.

10. The apparatus according to claim 1, wherein the plurality of nano-fingers extend substantially perpendicularly with respect to a plane of the substrate when the plurality of active material layers are electrostatically charged.

11. The apparatus according to claim 1, wherein the plurality of active material layers comprise Raman-active material layers to enhance Raman light emission from at least one molecule in an analyte disposed at least one of on and near the Raman-active material layers.

12. A surface enhanced Raman spectroscopy (SERS) system comprising:
    an apparatus for performing SERS, said apparatus comprising:
        a substrate;
        a plurality of flexible nano-fingers, each of the plurality of nano-fingers having a first end attached to the substrate, a free second end, and a body portion extending between the first end and the second end, wherein the plurality of nano-fingers are arranged in an array on the substrate; and
        a plurality of active material layers disposed on the second ends of the plurality of nano-fingers,
    a voltage source to selectively apply a voltage through an electrically conductive source that causes the plurality of active material layers to be selectively electrostatically charged, wherein the plurality of nano-fingers are to be in a substantially collapsed state in which the active material layers on at least two of the nano-fingers contact each other when the active material layers are under dominant attractive forces between the plurality of nano-fingers and wherein the active material layers are to repel each other when the plurality of active material layers are electrostatically charged;
    an illumination source to illuminate the plurality of nano-fingers to produce a Raman scattered light from an analyte located near the second ends; and
    a detector positioned to detect the Raman scattered light emitting from the analyte.

13. The SERS system according to claim 12, wherein the substrate comprises the electrically conductive source.

14. The SERS system according to claim 13, wherein each of the plurality of nano-fingers is formed of at least a semi-insulating material to thereby substantially limit or prevent conduction of electrical charge from the substrate to the plurality of active material layers.

15. The SERS system according to claim 12, wherein the voltage source is to modulate application of the voltage through the electrically conductive source at a defined frequency.

16. The SERS system according to claim 15, wherein the detector is to lock-in to the defined frequency of the voltage source to thereby improve a signal-to-noise ratio of the detected Raman scattered light.

17. The SERS system according to claim 12, wherein the plurality of nano-fingers are arranged sufficiently close to each other to cause the active material layers disposed on neighboring second ends to be attracted to contact each other under dominant attractive forces between the neighboring plurality of nano-fingers.

18. A method for performing surface enhanced Raman spectroscopy (SERS) to detect at least one analyte molecule on an apparatus having a plurality of flexible nano-fingers, each of the plurality of nano-fingers having a first end attached to a substrate, a free second end, and a body portion extending between the first end and the second end, wherein the plurality of nano-fingers are arranged in an array on the substrate, and wherein a plurality of active material layers are disposed on the second ends of the plurality of nano-fingers, said method comprising:

activating a voltage source to apply a voltage through an electrically conductive source to cause the active material layers to become electrostatically charged, wherein the active material layers disposed on the second ends are to repel each other when the active material layers are electrostatically charged and thereby create gaps between the active material layers into which an analyte is introducible;

deactivating the voltage source, wherein the plurality of nano-fingers are to be in a collapsed state in which the active layers on at least two of the nano-fingers contact each other when the voltage source is deactivated;

illuminating the plurality of nano-fingers to produce a Raman scattered light from the analyte; and detecting the Raman scattered light produced from the analyte.

19. The method according to claim 18, wherein activating and deactivating the voltage source further comprises modulating the activation and deactivation of the voltage source at a defined frequency to cause the plurality of active material layers on the second ends of the plurality of nano-fingers to modulate between being repelled from each other and contacting each other.

20. The method according to claim 19, wherein detecting the Raman scattered light further comprises detecting the Raman scattered light by locking into the defined frequency at which the voltage source is activated and deactivated to enhance a signal-to-noise ratio in the detection of the Raman scattered light.

\* \* \* \* \*